(12) United States Patent
Carola et al.

(10) Patent No.: US 8,052,963 B2
(45) Date of Patent: Nov. 8, 2011

(54) [(4-OXO-4H-CHROMEN-3-YL)HYDROXY-METHYL]- OR [(4-OXO-4H-CHROMEN-3-YL)METHYL]PHOSPHONIC ACID DERIVATIVES

(75) Inventors: Christophe Carola, Heidelberg (DE); Herwig Buchholz, Frankfurt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 301 days.

(21) Appl. No.: 12/447,369

(22) PCT Filed: Oct. 4, 2007

(86) PCT No.: PCT/EP2007/008589
§ 371 (c)(1),
(2), (4) Date: Apr. 27, 2009

(87) PCT Pub. No.: WO2008/052631
PCT Pub. Date: May 8, 2008

(65) Prior Publication Data
US 2010/0004209 A1    Jan. 7, 2010

(30) Foreign Application Priority Data
Oct. 28, 2006  (DE) .......................... 10 2006 050 925

(51) Int. Cl.
*A61Q 17/04*  (2006.01)
*A61K 31/665*  (2006.01)
*C07F 9/30*  (2006.01)
*C07F 9/32*  (2006.01)

(52) U.S. Cl. ............. 424/60; 424/59; 514/100; 549/218

(58) Field of Classification Search .................. 549/218; 424/59, 60; 514/100
See application file for complete search history.

(56) References Cited

FOREIGN PATENT DOCUMENTS

| JP | 55143908 A | 11/1980 |
|---|---|---|
| JP | 10237081 A | 9/1998 |
| JP | 10237081 W | 9/1998 |
| WO | 2008052631 R | 10/2006 |

OTHER PUBLICATIONS

Lejczak, B. et al. "Phosphonic and phosphinic acid analogues of tyrosine and 3, 4-dihydroxyphenylalanine (dopa) as potential antimelanotic agents." Anti-Cancer Drug Design 5 S. (1990): 351-358.

Budzisz, Elzbieta et al. "Synthesis, antimicrobal, and alkylating properties of 3-phosphonic derivatives of chromone." Arch. Pharm. Pharm. Med. Chem. 334, S. (2001): 381-387.

Kostka, Krzysztof and Roman Modranka. "The Synthesis of Chromone-3-Methanephosphonic Acid and Chromone-2-Methanephosphonic Acid." Phosphorus, Sulfur, and Silicon 57(1991): 279-285.

Sanchez-Moreno, Concepcion et al. "A Procedure to Measure the Antiradical Efficiency of Polyphenols." Journal of Science Food Agric. 76 (1998): 270-276.

*Primary Examiner* — Bernard Dentz
(74) *Attorney, Agent, or Firm* — Millen, White, Zelano & Branigan, P.C.

(57) ABSTRACT

The present invention relates to compounds of the formula (I), where $R^1$ to $R^3$ each, independently of one another, denote H, hydroxyl or alkoxy having 1 to 8 C atoms, $R^4$ denotes alkyl having 1 to 4 C atoms, H, hydroxyl or alkoxy having 1 to 8 C atoms, $R^5$ denotes H or hydroxyl, and $R^6$ denotes H or alkyl having 1 to 18 C atoms, or salts thereof, but where all $R^1$ to $R^4$ together cannot be equal to H, to compositions, and to the preparation and use thereof.

19 Claims, No Drawings

[(4-OXO-4H-CHROMEN-3-YL)HYDROXY-METHYL]- OR [(4-OXO-4H-CHROMEN-3-YL) METHYL]PHOSPHONIC ACID DERIVATIVES

The present invention relates to [(4-oxo-4H-chromen-3-yl) hydroxymethyl]- or [(4-oxo-4H-chromen-3-yl)methyl]phosphonic acid, derivatives thereof and/or salts thereof, to compositions and mixtures comprising these compounds, and to the preparation and use thereof.

An area of application of the compounds according to the invention is, for example, cosmetics. The object of care cosmetics is wherever possible to obtain the impression of youthful skin. In principle, there are various ways of achieving this object. For example, existing skin damage, such as irregular pigmentation or the formation of wrinkles, can be compensated for by covering powders or creams. Another approach is to protect the skin against environmental influences which lead to permanent damage and thus ageing of the skin. The idea is therefore to intervene in a preventative manner and thus to delay the ageing process. An example of this are the UV filters already mentioned, which, as a result of absorption of certain wavelength ranges, prevent or at least reduce skin damage. Whereas in the case of UV filters the damaging event, the UV radiation, is screened off by the skin, another route involves attempting to support the skin's natural defence or repair mechanisms against the damaging event. Finally, a further approach involves compensating for the weakening of the defence functions of the skin against harmful influences with increasing age by externally supplying substances which are able to replace this diminishing defence or repair function. For example, the skin has the ability to scavenge free radicals generated by external or internal stress factors. This ability diminishes with increasing age, causing the ageing process to accelerate with increasing age.

A certain degree of tanning of the skin is regarded in modern society as attractive and as an expression of vigour and sportiness. In addition to this desired action of the sun on the skin, a number of undesired side effects occur, such as sunburn or premature skin ageing and wrinkling. Of particular importance here is the wavelength range from 280 to 400 nm. This range covers UV-B rays having a wavelength of between 280 and 320 nm, which play a crucial role in the formation of solar erythema, and also UV-A rays having a wavelength of between 320 and 400 nm, which tan the skin, but also allow ageing, favour the triggering of an erythematous reaction or can exacerbate this reaction in certain people or even trigger phototoxic or photoallergic and irritative reactions.

Skin damage is not caused just by sunlight, but also by other external influences, such as cold or heat. Furthermore, the skin undergoes natural ageing, with the formation of wrinkles and a reduction in the elasticity of the skin.

A further difficulty in the preparation of cosmetics is that active compounds which are intended to be incorporated into cosmetic compositions are frequently unstable and can be damaged in the composition. The damage may be caused, for example, by a reaction with atmospheric oxygen or by absorption of UV rays. The molecules damaged in this way may, for example, change their colour and/or lose their activity through their structural change.

A known way of dealing with the problems described consists in adding antioxidants to the compositions.

According to C D Römpp Chemie Lexikon [C D Römpp's Lexicon of Chemistry]—Version 1.0, Stuttgart/New York: Georg Thieme Verlag 1995, antioxidants are compounds which inhibit or prevent undesired changes in the substances to be protected caused by the action of oxygen, inter alia oxidative processes. Areas of application are, for example, in plastics and rubber for protection against ageing; in fats for protection against rancidity, in oils, cattle feeds, automotive gasoline and jet fuels for protection against gumming, in transformer and turbine oil against sludge formation, in flavours against odour impairment. Compounds that are effective as antioxidants are, inter alia, phenols, hydroquinones, pyrocatechols and aromatic amines, each of which are substituted by sterically hindering groups, and metal complexes thereof. According to Römpp, the action of the antioxidants usually consists in that they act as free-radical scavengers for the free radicals which arise during autoxidation.

There therefore continues to be a demand for skin-tolerated antioxidants which are also suitable for use in skin-care compositions and can be incorporated in a suitable manner into cosmetic compositions.

The object of the invention is therefore to provide compounds which, applied in cosmetic compositions, can exert a protective action against oxidative stress on body cells and/or counter skin ageing.

Surprisingly, it has been found that [(4-oxo-4H-chromen-3-yl)hydroxy-methyl]- or [(4-oxo-4H-chromen-3-yl)methyl] phosphonic acid, derivatives thereof or salts thereof are highly suitable as antioxidants on the human skin.

To date, unsubstituted chromone-3-methanephosphonic acids and methyl, ethyl, isopropyl and n-butyl esters thereof are known. However, Kostka et al., Phosphorus, Sulfur and Silicon and the Related Elements (1991), 57 (3-4), 279-85, describe merely the synthesis of these compounds.

The present invention therefore relates firstly to compounds of the formula I

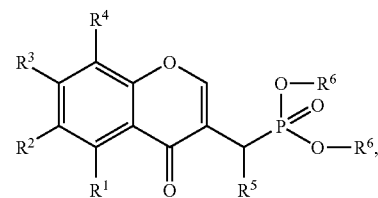

where
$R^1$ to $R^3$ each, independently of one another, denote H, hydroxyl or alkoxy having 1 to 8 C atoms,
$R^4$ denotes alkyl having 1 to 4 C atoms, H, hydroxyl or alkoxy having 1 to 8 C atoms,
$R^5$ denotes H or hydroxyl, and
$R^6$ denotes H or alkyl having 1 to 18 C atoms,
or salts thereof, but where all $R^1$ to $R^4$ together cannot be equal to H.

In formula I, alkoxy having 1 to 8 C atoms denotes, for example, methoxy, ethoxy, propoxy, butoxy, pentoxy, hexoxy, heptoxy or octoxy, where in each case the isomeric representatives of the alkyl groups may also be bonded via an oxygen.

In formula I, alkyl having 1 to 18 C atoms denotes, for example, methyl, ethyl, n-propyl, isopropyl, n-butyl, sec-butyl, tert-butyl, n-$C_5H_{11}$ to n-$C_{18}H_{37}$, and isomeric forms thereof. Alkyl having 1 to 5 C atoms is, for example, methyl, ethyl, n-propyl, isopropyl, n-butyl, sec-butyl, tert-butyl or n-pentyl.

$R^1$ to $R^3$ are preferably each, independently of one another, H, hydroxyl, methoxy or ethoxy, particularly preferably H or hydroxyl.

$R^4$ is preferably H, methyl, ethyl or hydroxyl, particularly preferably methyl or hydroxyl.

$R^1$ is very particularly preferably H.

$R^2$ and $R^3$ are each, independently of one another, very particularly preferably hydroxyl.

$R^5$ is very particularly preferably hydroxyl.

$R^6$ is particularly preferably H or alkyl having 1 to 5 C atoms, very particularly preferably H or methyl.

The present invention furthermore relates, corresponding to the preferred use of the compounds according to the invention, to a composition comprising at least one compound of the formula I.

The salts are preferably those with counterions which do not hinder incorporation of the compounds of the formula I into compositions. For example, it is preferred for them to be alkali metal, alkaline-earth metal or ammonium salts. It is particularly preferred in accordance with the invention for the salts to be sodium, potassium, magnesium or ammonium salts, for example triethanolammonium salts.

Advantages of the compounds or compositions according to the invention are, in particular, the antioxidant action and the good toleration by the skin. Of particular advantage is the particular action profile of the compounds to be employed in accordance with the invention, which is evident through stability of the compounds in the compositions and antioxidant action in or on the skin.

Owing to these properties, the present invention relates to the use of the compounds of the formula I, as indicated above, as antioxidants or for the preparation of a composition, in particular having antioxidant properties, or for the preparation of compositions which can exert a protective action against oxidative stress on body cells and/or can counter ageing of the skin or can contribute to a reduction in the consequences of skin ageing.

The compositions here are usually either compositions which can be applied topically, for example cosmetic, pharmaceutical or dermatological formulations, or foods or food supplements. In this case, the compositions comprise a cosmetically, pharmaceutically or dermatologically or food-suitable vehicle and, depending on the desired property profile, optionally further suitable ingredients.

The topical compositions are preferably employed as cosmetic or dermatological compositions.

For the purposes of the present invention, the term composition or formulation is used synonymously.

The compounds of the formula I are, in accordance with the invention, typically employed in amounts of 0.01% by weight to 20% by weight, preferably in amounts of 0.1% by weight to 10% by weight and particularly preferably in amounts of 1% by weight to 8% by weight. The person skilled in the art is presented with absolutely no difficulties here in selecting the amounts correspondingly depending on the intended action of the composition.

In order that the compounds of the formula I are able to develop their positive action as free-radical scavengers on the skin particularly well, it may be preferred to allow the compounds of the formula I to penetrate into deeper skin layers. Several possibilities are available for this purpose, for example corresponding transport agents, for example liposomes, which enable transport of the compounds of the formula I through the outer skin layers, may also be provided in the composition. Finally, systemic transport of the compounds of the formula I is also conceivable. The composition is then designed, for example, in such a way that it is suitable for oral administration.

In general, the substances of the formula I act as free-radical scavengers. Free radicals of this type are generated not only by sunlight, but are formed under various conditions. Examples are anoxia, which blocks the flow of electrons upstream of the cytochrome oxidases and causes the formation of superoxide free-radical anions; inflammation associated, inter alia, with the formation of superoxide anions by the membrane NADPH oxidase of the leukocytes, but also associated with the formation (through disproportionation in the presence of iron(II) ions) of the hydroxyl free radicals and other reactive species which are normally involved in the phenomenon of phagocytosis; and lipid autoxidation, which is generally initiated by a hydroxyl free radical and produces lipidic alkoxy free radicals and hydroperoxides.

It is thought that preferred compounds of the formula I also act as enzyme inhibitors. They are thought to inhibit histidine decarboxylase, protein kinases, elastase, aldose reductase and hyaluronidase, and therefore enable the intactness of the basic substance of vascular sheaths to be maintained. Furthermore, they are thought to inhibit non-specifically catechol O-methyl transferase, causing the amount of available catecholamines and thus the vascular strength to be increased. Furthermore, they inhibit AMP phosphodiesterase, giving the substances potential for inhibiting thrombocyte aggregation.

Owing to these properties, the compounds or compositions according to the invention are generally suitable for immune protection and for the protection of DNA and RNA. In particular, the compositions are suitable for the protection of DNA and RNA against oxidative attack, against free radicals and against damage due to radiation, in particular UV radiation. A further advantage of the compositions according to the invention is cell protection, in particular protection of Langerhans cells against damage due to the above-mentioned influences. All these uses and the use of the compounds of the formula I for the preparation of compositions which can be employed correspondingly are expressly also a subject-matter of the present invention.

In particular, preferred compositions according to the invention are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leukoplakia, leukoplakiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammation which is not associated with a defect in keratinisation, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in sebum production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, for the treatment of skin problems caused by UV radiation.

The antioxidative actions of the compounds of the formula I can be demonstrated, for example, by means of the 2,2-diphenyl-1-picrylhydrazyl (DPPH) assay. 2,2-Diphenyl-1-picrylhydrazyl is a free radical which is stable in solution. The unpaired electron results in a strong absorption band at 515 nm; the solution has a dark-violet colour. In the presence of a free-radical scavenger, the electron is paired, the absorption disappears, and the decoloration proceeds stoichiometrically taking into account the electrons taken up. The absorbance is measured in a photometer. The anti-free-radical property of the substance to be tested is determined by measuring the concentration at which 50% of the 2,2-diphenyl-1-picrylhydrazyl employed has reacted with the free-radical scavenger. This concentration is expressed as $EC_{50}$, a value which should be regarded as a property of the substance under the given measurement conditions. The substance investigated is compared with a standard (for example tocopherol). The $EC_{50}$ value here is a measure of the capacity of the respective compound to scavenge free radicals. The lower the $EC_{50}$ value, the higher the capacity to scavenge free radicals. A further important aspect for the action of the antioxidants is the time in which this $EC_{50}$ value is achieved. This time, measured in minutes, gives the $T_{EC50}$ value, which allows a conclusion to be drawn on the rate at which these antioxidants scavenge free radicals. For the purposes of these inventions, antioxidants which achieve this value within less than 60 minutes are regarded as fast, those which only achieve the $EC_{50}$ value after more than 120 minutes are regarded as having a time-delayed action.

The anti-free-radical efficiency (AE) (described in C. Sanchez-Moreno, J. A. Larrauri and F. Saura-Calixto in J. Sci. Food Agric. 1998, 76(2), 270-276) is given by the abovementioned quantities in accordance with the following relationship:

$$AE = \frac{1}{EC_{50} T_{EC50}}$$

A low AE ($\times 10^{-3}$) is in the range up to about 10, a moderate AE is in the range from 10 to 20 and a high AE has in accordance with the invention values above 20.

It may be particularly preferred in accordance with the invention to combine fast-acting antioxidants with those having a slow or time-delayed action. Typical per cent by weight ratios of the fast-acting antioxidants to time-delayed antioxidants are in the range 10:1 to 1:10, preferably in the range 10:1 to 1:1, and for skin-protecting compositions particularly preferably in the range 5:1 to 2:1. In other compositions which are likewise preferred in accordance with the invention, however, it may be advantageous for the purposes of action optimisation for more time-delayed antioxidants than fast-acting antioxidants to be present. Typical compositions then exhibit per cent by weight ratios of the fast-acting anti-oxidants to time-delayed anti-oxidants in the range 1:1 to 1:10, preferably in the range 1:2 to 1:8.

The protective action against oxidative stress or against the effect of free radicals can thus be further improved if the compositions comprise one or more further antioxidants, the person skilled in the art being presented with absolutely no difficulties in selecting suitably fast-acting or time-delayed anti oxidants.

In a preferred embodiment of the present invention, the composition is therefore a composition for the protection of body cells against oxidative stress, in particular for reducing skin ageing, characterised in that it preferably comprises one or more further antioxidants besides the one or more compounds of the formula I.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), and also (metal) chelating agents (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nor-dihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Suitable antioxidants are also compounds of the general formula A or B

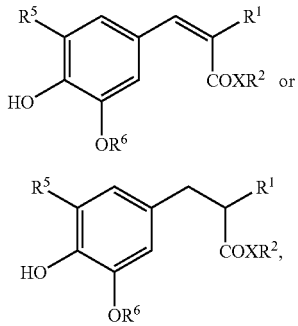

in which
R$^1$ can be selected from the group —C(O)CH$_3$, —CO$_2$R$^3$, —C(O)NH$_2$ and —C(O)N(R$^4$)$_2$,
X denotes O or NH,
R$^2$ denotes linear or branched alkyl having 1 to 30 C atoms,
R$^3$ denotes linear or branched alkyl having 1 to 20 C atoms,
R$^4$ in each case, independently of one another, denotes H or linear or branched alkyl having 1 to 8 C atoms,
R$^5$ denotes linear or branched alkyl having 1 to 8 C atoms or linear or branched alkoxy having 1 to 8 C atoms, and
R$^6$ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene)malonate (for example Oxynex® ST Liquid) and/or bis(2-ethylhexyl) 2-(4-hydroxy-3,5-dimethoxy-benzyl)malonate (for example RonaCare® AP).

Mixtures of antioxidants are likewise suitable for use in the cosmetic compositions according to the invention. Known and commercial mixtures are, for example, mixtures comprising, as active compounds, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Anti-oxidants of this type are usually employed in such compositions with compounds of the formula I in per cent by weight ratios in the range from 1000:1 to 1:1000, preferably in per cent by weight ratios of 100:1 to 1:100.

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin B$_1$), riboflavin (vitamin B$_2$), nicotinamide, vitamin C (ascorbic acid), vitamin D, ergocalciferol (vitamin D$_2$), vitamin E, DL-α-tocopherol, tocopherol E acetate, tocopherol hydrogensuccinate, vitamin K$_1$, esculin (vitamin P active compound), thiamine (vitamin B$_1$), nicotinic acid (niacin), pyridoxine, pyridoxal, pyridoxamine (vitamin B$_6$), pantothenic acid, biotin, folic acid and cobalamine (vitamin B$_{12}$), particularly preferably vitamin A palmitate, vitamin C and derivatives thereof, DL-α-tocopherol, tocopherol E acetate, nicotinic acid, pantothenic acid and biotin. Vitamins are usually employed here with compounds of the formula I in per cent by weight ratios in the range from 1000:1 to 1:1000, preferably in per cent by weight ratios of 100:1 to 1:100.

Compositions which are particularly preferred in accordance with the invention also comprise pure UV filters in addition to the compounds of the formula I.

On use of the dibenzoylmethane derivatives, which are particularly preferred as UV-A filters, in combination with the compounds of the formula I, an additional advantage arises: the UV-sensitive dibenzoylmethane derivatives are additionally stabilised by the presence of the compounds of the formula I. The present invention therefore furthermore relates to the use of the compounds of the formula I for the stabilisation of dibenzoylmethane derivatives in compositions.

In principle, all UV filters are suitable for combination with the compounds of the formula I according to the invention. Particular preference is given to UV filters whose physiological acceptability has already been demonstrated. Both for UVA and UVB filters, there are many proven substances known from the specialist literature, for example
benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]-benzyl}acrylamide (for example Mexoryl® SW), N,N,N-trimethyl-4-(2-oxoborn-3-ylidenemethyl)anilinium methylsulfate (for example Mexoryl® SK) or (2-oxoborn-3-ylidene)toluene-4-sulfonic acid (for example Mexoryl® SL),
benzoyl- or dibenzoylmethanes, such as 1-(4-tert-butylphenyl)-3-(4-methoxyphenyl)propane-1,3-dione (for example Eusolex® 9020) or 4-isopropyl-dibenzoylmethane (for example Eusolex® 8020),
benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40),
methoxycinnamic acid esters, such as octyl methoxycinnamate (for example Eusolex® 2292), isopentyl 4-methoxycinnamate, for example as a mixture of the isomers (for example Neo Heliopan® E 1000),
salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS),
4-aminobenzoic acid and derivatives, such as 4-aminobenzoic acid, 2-ethylhexyl 4-(dimethylamino)benzoate (for example Eusolex® 6007), ethoxylated ethyl 4-aminobenzoate (for example Uvinul® P25),
phenylbenzimidazolesulfonic acids, such as 2-phenylbenzimidazole-5-sulfonic acid and potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1,4-phenylene)bisbenzimidazole-6-sulfonic acid,
and further substances, such as
2-ethylhexyl 2-cyano-3,3-diphenylacrylate (for example Eusolex® OCR),
3,3'-(1,4-phenylenedimethylene)bis(7,7-dimethyl-2-oxobicyclo[2.2.1]hept-1-ylmethanesulfonic acid and salts thereof (for example Mexoryl® SX),
2,4,6-trianilino-(p-carbo-2'-ethylhexyl-1'-oxy)-1,3,5-triazine (for example Uvinul® T 150), hexyl 2-(4-diethylamino-2-hydroxybenzoyl)benzoate (for example Uvinul®UVA Plus, BASF).

The compounds mentioned in the list should only be regarded as examples. It is of course also possible to use other UV filters.

These organic UV filters are generally incorporated into cosmetic formulations in an amount of 0.5 to 10 per cent by weight, preferably 1-8% by weight.

Further suitable organic UV filters are, for example, 2-(2H-benzotriazol-2-yl)-4-methyl-6-(2-methyl-3-(1,3,3,3-tetramethyl-1-(trimethylsilyloxy)disiloxanyl)propyl) phenol (for example Silatrizole®), α-(trimethylsilyl)-ω-[trimethylsilyl)oxy]poly[oxy(dimethyl [and approximately 6% of methyl[2-[p-[2,2-bis (ethoxycarbonyl]vinyl]phenoxy]-1-methyleneethyl] and approximately 1.5% of methyl[3-[p-[2,2-bis (ethoxy-carbonyl)vinyl)phenoxy)propenyl) and 0.1 to 0.4% of (methylhydrogen]-silylene]] (n≈60) (CAS No. 207 574-74-1), 2,2'-methylenebis(6-(2H-benzotriazol-2-yl)-4-(1,1,3,3-tetramethylbutyl)-phenol) (CAS No. 103 597-45-1), 2,2'-(1,4-phenylene)bis(1H-benzimidazole-4,6-disulfonic acid, mono-sodium salt) (CAS No. 180 898-37-7)

2,4-bis{[4-(2-ethylhexyloxy)-2-hydroxy]phenyl}-6-(4-methoxyphenyl)-1,3,5-triazine (CAS No. 103 597-45-, 187 393-00-6), 2-ethyl hexyl 4,4'-[(6-[4-((1,1-dimethylethyl)aminocarbonyl)phenylamino]-1,3,5-triazine-2,4-diyl)diimino]bis (benzoate) (for example Uvasorb® HEB).

Organic UV filters are generally incorporated into cosmetic formulations in an amount of 0.5 to 20 per cent by weight, preferably 1-15% by weight.

Conceivable inorganic UV filters are those from the group of the titanium dioxides, such as, for example, coated titanium dioxide (for example Eusolex® T-2000, Eusolex® T-AQUA), zinc oxides (for example Sachtotec®), iron oxides or also cerium oxides. These inorganic UV filters are generally incorporated into cosmetic compositions in an amount of 0.5 to 20 per cent by weight, preferably 2-10% by weight.

Preferred compounds having UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and potassium, sodium and triethanolamine salts thereof.

Combination of one or more of the compounds of the formula I with further UV filters enables the protective action against damaging effects of UV radiation to be optimised.

Optimised compositions may comprise, for example, the combination of the organic UV filters 4'-methoxy-6-hydroxyflavone with 1-(4-tert-butylphenyl)-3-(4-methoxyphenyl) propane-1,3-dione and 3-(4'-methylbenzylidene)-dl-camphor. This combination gives rise to broad-band protection, which can be supplemented by the addition of inorganic UV filters, such as titanium dioxide microparticles.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables composition problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active compound (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules particularly preferably to be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules in compositions according to the invention are preferably present in amounts which ensure that the encapsulated UV filters are present in the composition in the above-indicated amounts.

The compositions according to the invention may in addition comprise further conventional skin-protecting or skin-care active compounds. These may in principle be any active compounds known to the person skilled in the art.

Particularly preferred active compounds are pyrimidinecarboxylic acids and/or aryl oximes.

Pyrimidinecarboxylic acids occur in halophilic microorganisms and play a role in osmoregulation of these organisms (E. A. Galinski et al., Eur. J. Biochem., 149 (1985) pages 135-139). Of the pyrimidinecarboxylic acids, particular mention should be made here of ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoine and ectoine derivatives, such as hydroxyectoine, can advantageously be used in medicaments. In particular, hydroxyectoine can be employed for the preparation of a medicament for the treatment of skin diseases. Other areas of application of hydroxyectoine and other ectoine derivatives are typically in areas in which, for example, trehalose is used as additive. Thus, ectoine derivatives, such as hydroxyectoine, can be used as protectant in dried yeast and bacteria cells. Pharmaceutical products, such as non-glycosylated, pharmaceutically active peptides and proteins, for example t-PA, can also be protected with ectoine or its derivatives.

Of the cosmetic applications, particular mention should be made of the use of ectoine and ectoine derivatives for the care of aged, dry or irritated skin. Thus, European patent application EP-A-0 671 161 describes, in particular, that ectoine and hydroxyectoine are employed in cosmetic compositions, such as powders, soaps, surfactant-containing cleansing products, lipsticks, rouge, make-up, care creams and sunscreen preparations.

Preference is given here to the use of a pyrimidinecarboxylic acid of the following formula C

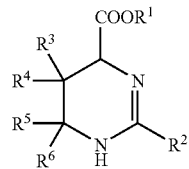

C in which $R^1$ is a radical H or $C_{1-8}$-alkyl, $R^2$ is a radical H or $C_{1-4}$-alkyl, and $R^3$, $R^4$, $R^5$ and $R^6$ are each, independently of one another, a radical from the group H, OH, $NH_2$ and $C_{1-4}$-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoine ((S)-1,4,5,6-tetrahydro-2-methyl-4-pyrimidine-carboxylic acid) and hydroxyectoine ((S,S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight. The pyrimidinecarboxylic acids are preferably employed here in per cent by weight ratios of 100:1 to 1:100 with respect to the compounds of the formula I, with per cent by weight ratios in the range 1:10 to 10:1 being particularly preferred.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are associated with inflammation. It is known that compositions of this type can be used, for example, for the therapy of psoriasis, various forms of eczema, irritative and toxic dermatitis, UV dermatitis and further allergic and/or inflammatory diseases of the skin and skin appendages. Compositions according to the invention which, in addition to the compound of the formula I, additionally comprise an aryl oxime, preferably 2-hydroxy-5-methyllaurophenone oxime, exhibit surprising anti-inflammatory suitability. The compositions here preferably comprise 0.01% by weight to 10% by weight of the aryl oxime, it being particularly preferred for the composition to comprise 0.05 to 5% by weight of aryl oxime.

All compounds or components which can be used in the compositions are either known and commercially available or can be synthesised by known processes.

The one or more compounds of the formula I can be incorporated into cosmetic or dermatological compositions in a conventional manner. Suitable compositions are those for external use, for example in the form of a cream, lotion, gel or as a solution which can be sprayed onto the skin. Suitable for internal use are administration forms such as capsules, coated tablets, powders, tablet solutions or solutions.

Examples which may be mentioned of use forms of the compositions according to the invention are: solutions, suspensions, emulsions, PIT emulsions, pastes, ointments, gels, creams, lotions, powders, soaps, surfactant-containing cleansing preparations, oils, aerosols and sprays. Examples of other use forms are sticks, shampoos and shower compositions. Any desired customary vehicles, auxiliaries and, if desired, further active compounds may be added to the composition.

Preferred auxiliaries originate from the group of the preservatives, stabilisers, solubilisers, colorants, odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eye shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other lipids, as well as water and an emulsifier, as usually used for a composition of this type.

The lipid phase may advantageously be selected from the following group of substances:
mineral oils, mineral waxes;
oils, such as triglycerides of capric or caprylic acid, furthermore natural oils, such as, for example, castor oil;
fats, waxes and other natural and synthetic lipids, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of the esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of the esters of aromatic carboxylic acids and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethyl-hexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of the branched and unbranched hydrocarbons and hydrocarbon waxes, silicone oils, dialkyl ethers, or the group of the saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18, C atoms. The fatty acid triglycerides may advantageously be selected, for example, from the group of the synthetic, semi-synthetic and natural oils, for example olive oil, sunflower oil, soya oil, peanut oil, rape-seed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group 2-ethylhexyl isostearate, octyldodecanol, isotridecyl isononanoate, isoeicosane, 2-ethyl-hexyl cocoate, $C_{12-15}$-alkyl benzoate, caprylic/capric acid triglyceride, dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane, poly(methylphenylsiloxane).

Also particularly advantageous are mixtures of cyclomethicone and isotridecyl isononanoate and of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other lipids, as well as water and an emulsifier, as usually used for a formulation of this type.

In a preferred embodiment, the compositions according to the invention comprise hydrophilic surfactants.

The hydrophilic surfactants are preferably selected from the group of the alkylglucosides, acyl lactylates, betaines and coconut amphoacetates.

The alkylglucosides are themselves advantageously selected from the group of the alkylglucosides which are distinguished by the structural formula

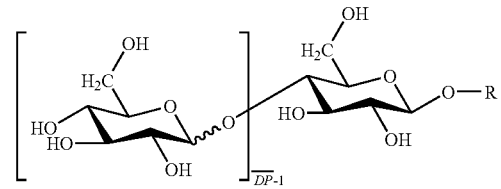

where R represents a branched or unbranched alkyl radical having 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \sum \frac{p_i}{100} \cdot i$$

in which $p_1$, $p_2$, $p_3$ ... $p_i$ represent the proportion of mono-, di-, tri- ... i-fold glucosylated products in per cent by weight. Advantageous in accordance with the invention is the selection of products having degrees of glucosylation of 1-2, particularly advantageously of 1.1 to 1.5, very particularly advantageously of 1.2-1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglycosides which are particularly advantageously used in accordance with the invention are selected from the group octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and auxiliaries or mixtures which are distinguished by an effective content of the active compounds used in accordance with the invention, for example Plantaren® 1200 (Henkel KGaA), Oramix® NS 10 (Seppic).

The acyllactylates are themselves advantageously selected from the group of the substances which are distinguished by the structural formula

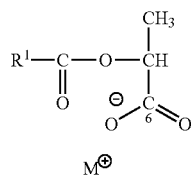

where $R^1$ denotes a branched or unbranched alkyl radical having 1 to 30 carbon atoms, and $M^+$ is selected from the group of the alkali metal ions and the group of ammonium ions which are substituted by one or more alkyl and/or one or more hydroxyalkyl radicals, or corresponds to half an equivalent of an alkaline-earth metal ion.

For example, sodium isostearyl lactylate, for example the product Pathionic® ISL from the American Ingredients Company, is advantageous.

The betaines are advantageously selected from the group of the substances which are distinguished by the structural formula

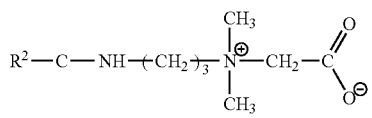

where $R^2$ denotes a branched or unbranched alkyl radical having 1 to 30 carbon atoms.

$R^2$ particularly advantageously denotes a branched or unbranched alkyl radical having 6 to 12 carbon atoms.

For example, capramidopropylbetaine, for example the product Tego® Betain 810 from Th. Goldschmidt AG, is advantageous.

A coconut amphoacetate which is advantageous in accordance with the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions according to the invention are applied to the skin and/or the hair in an adequate amount in the usual manner for cosmetics.

Cosmetic and dermatological compositions according to the invention can exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous in accordance with the invention are, for example, O/W emulsifiers, principally from the group of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group of the ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can be used is advantageously sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageously employed in accordance with the invention are the following:
fatty alcohols having 8 to 30 carbon atoms, monoglycerol esters of saturated and/or unsaturated, branched and/or unbranched alkanecarboxylic acids having a chain length of 8 to 24, in particular 12-18, C atoms, diglycerol esters of saturated and/or unsaturated, branched and/or unbranched alkanecarboxylic acids having a chain length of 8 to 24, in particular 12-18, C atoms, monoglycerol ethers of saturated and/or unsaturated, branched and/or unbranched alcohols having a chain length of 8 to 24, in particular 12-18, C atoms, diglycerol ethers of saturated and/or unsaturated, branched and/or unbranched alcohols having a chain length of 8 to 24, in particular 12-18, C atoms, propylene glycol esters of saturated and/or unsaturated, branched and/or unbranched alkanecarboxylic acids having a chain length of 8 to 24, in particular 12-18, C atoms, and sorbitan esters of saturated and/or unsaturated, branched and/or unbranched alkanecarboxylic acids having a chain length of 8 to 24, in particular 12-18, C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG 30 dipolyhydroxystearate.

Compositions which are preferred in accordance with the invention are particularly suitable for protecting human skin against ageing processes and against oxidative stress, i.e. against damage caused by free radicals, as are generated, for example, by solar irradiation, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dyes used are preferably approved dyes which are listed in the Cosmetics Regulation, Annex 3, as positive list.

The preservatives used are preferably approved preservatives which are listed in the Cosmetics Regulation, Annex 6, as positive list or also anti-microbial pigments, as described, for example, in WO 2004/0092283 or WO 2004/091567.

Suitable preservatives are therefore also alkyl esters of p-hydroxybenzoic acid, hydantoin derivatives, propionate salts or a multiplicity of ammonium compounds.

Very particularly preferred preservatives are methylparaben, propylparaben, imidazolidinylurea, sodium dehydroxyacetate or benzyl alcohol. Preservatives are employed in amounts between 0.5 and 2% by weight.

Emollients or softeners are often incorporated into cosmetic compositions. They are preferably employed in 0.5 to 50% by weight, preferably between 5 and 30% by weight, based on the composition as a whole. In general, softeners can be classified in classes, such as, for example, the category of the esters, fatty acids or fatty alcohols, polyols, hydrocarbons and oils containing at least one amide structural unit.

Representative oils containing at least one amide structural unit together with their synthesis are described, in particular, in EP 1044676 and EP 0928608. A compound which is particularly preferably indicated is isopropyl N-lauroylsarcosinate, which is commercially available from Ajinomoto under the product name Eldew SL-205.

Of the esters, mono- or diesters can be selected. Examples in this respect are dibutyl adipate, diethyl sebacate, diisopropyl dimerate or dioctyl succinate. Branched fatty acid esters are, for example, 2-ethylhexyl myristate, isopropyl stearate or isostearyl palmitate. Tribasic esters are, for example, triisopropyl trilinoleate or trilauryl citrate. Straight-chain fatty acid esters are, for example, lauryl palmitate, myristyl lactate, oleyl erucate or stearyl oleate. Preferred esters are Coco-Caprylate/Caprate (=INCI name, these are esters of coconut fatty alcohols with saturated medium-chain fatty acids), propylene glycol myristyl ether acetate, diisopropyl adipate or cetyl octanoate.

Suitable fatty alcohols and acids are compounds which have 10 to 20 C atoms. Particularly preferred compounds are cetyl, myristyl, palmitic or stearic alcohol or acid.

Suitable polyols are linear or branched-chain alkylpolyhydroxyl compounds, for example propylene glycol, sorbitol or glycerol. However, it is also possible to employ polymeric polyols, for example polypropylene glycol or polyethylene glycol. Butylene glycol and propylene glycol are also particularly suitable compounds for enhancing the penetration capacity.

Examples of hydrocarbons as softeners are compounds which generally have 12 to 30 C atoms. Specific examples are arylalkyl benzoates, alkyl benzoates, mineral oils, Vaseline, squalenes or isoparaffins.

Further emollients or hydrophobicising agents are preferably $C_{12}$ to $C_{15}$ alkyl benzoates, dioctyl adipate, octyl stearate, octyldodecanol, hexyl laurate, octyldodecyl neopentanoate, cyclomethicone, dicaprylic ether, dimethicone, phenyltrimethicone, isopropyl myristate, caprylic/capric glycerides, propylene glycol dicaprylate/dicaprate or decyl oleate.

A further category of functional ingredients of cosmetic compositions in the sense of the invention are thickeners. Thickeners are generally employed in amounts between 0.1 and 20% by weight, preferably between 0.5 and 10% by weight, based on the total amount. Examples of these compounds are crosslinked polyacrylate materials, commercially available from B. F. Goodrich Company under the trade name Carbopol. It is also possible to use thickeners such as xanthan gum, carrageenan gum, gelatine gum, karaya gum, pectin gum or carob seed flour.

Under certain circumstances, it is possible for a compound to be both a thickener and also a softener. Examples thereof are silicone gums (kinematic viscosity>10 centistokes), esters, such as, for example, glycerol stearate, or cellulose derivatives, for example hydroxypropylcellulose.

The dispersant or solubiliser used can be an oil, wax or other lipid, a lower monoalcohol or lower polyol or mixtures thereof. Particularly preferred monoalcohols or polyols include ethanol, i-propanol, propylene glycol, glycerol and sorbitol.

A preferred embodiment of the invention is an emulsion in the form of a protective cream or milk which, in addition to the compound(s) of the formula I, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other lipids.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling and treating the hair, in the form of a lotion or gel for brushing or blow-waving, in the form of a hair lacquer, permanent waving composition, colorant or bleach for the hair. Besides the compound(s) of the formula I, the composition may comprise various adjuvants used in this type of composition, such as surface-active agents, thickeners, polymers, softeners, preservatives, foam stabilisers, electrolytes, organic solvents, silicone derivatives, oils, waxes, anti-grease agents, dyes and/or pigments which colour the composition itself or the hair, or other ingredients usually used for hair care.

The compositions, as described above, may include or comprise, essentially consist of or consist of the said necessary or optional constituents. All compounds or components which can be used in the compositions are either known and commercially available or can be synthesised by known methods.

The present invention furthermore relates to a process for the preparation of a composition which is characterised in that at least one compound of the formula I containing radicals as described above is mixed with a vehicle which is suitable cosmetically, pharmaceutically or dermatologically or for foods, and to the use of a compound of the formula I for the preparation of a composition, in particular having antioxidant properties.

The compositions according to the invention can be prepared with the aid of techniques which are well known to the person skilled in the art.

The mixing can result in dissolution, emulsification or dispersion of the compound of the formula I in the vehicle.

The invention also relates to a process for the preparation of the compounds of the formula I, where $R^6$, independently of one another, denotes alkyl having 1 to 18 C atoms, preferably alkyl having 1 to 5 C atoms, particularly preferably methyl, and $R^5$=OH, characterised in that a compound of the formula II

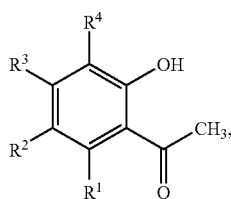

where $R^1$ to $R^4$ can have one of the meanings mentioned above, is reacted with a reagent selected from $POCl_3$, phosgene or trifluorosulfonic anhydride and an arylalkyl-, diaryl- or dialkylformamide to give an intermediate of the formula III

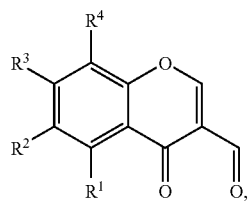

where $R^1$ to $R^4$ can have one of the meanings mentioned above, and this is subsequently reacted with a dialkyl phosphonate.

The alkyl groups of the dialkyl phosphonate form $R^6$.

The reaction to give the intermediates of the formula III, as described above, is also known as the Vilsmeier reaction.

Examples of arylalkyl-, diaryl- or dialkylformamides are N-phenyl-N-methylformamide, N,N-diphenylformamide, N,N-dimethylformamide, N,N-diethylformamide, N,N-dibutylformamide. It is also possible to employ N,N-formylpiperidine instead of a formamide.

The Vilsmeier reaction is preferably carried out in the presence of $POCl_3$ and dimethylformamide.

The Vilsmeier reaction is preferably carried out under inert-gas conditions. $POCl_3$ or another reagent from the group indicated is advantageously introduced at temperatures <5° C. The actual reaction temperature is between −50 and 75° C., preferably between −20 and 30° C. The reaction is particularly preferably carried out at room temperature.

The reaction of the intermediates of the formula III with dialkyl phosphonates is preferably carried out under inert-gas conditions and at reaction temperatures between 20 and 100° C., preferably between 25 and 85° C. The catalyst employed can be, for example, a trialkyl phosphite, CsF, KF, DBU (diazabicycloundec-7-ene), sodium, sodium methoxide, triethylamine or also NaOH, but where a further phase-transfer catalyst is required in the case of the use of NaOH. A trialkyl phosphite is preferably employed.

The alkyl groups of the trialkyl phosphite are preferably identical to the alkyl groups of the dialkyl phosphonate and stand for $R^6$ in the compounds of the formula I with the associated disclosed meanings.

Ester hydrolysis, for example by reaction with hydrochloric acid, gives compounds of the formula I in which $R^6$ in each case denotes H.

In a subsequent reduction step, for example by reduction using hydroiodic acid in the presence of red phosphorus, compounds of the formula I in which $R^5$ denotes H can be obtained.

The reduction is carried out, for example, in acetic acid at temperatures between 10 and 150° C., preferably between 20 and 125° C., particularly preferably at 100 to 120° C.

The conversion into salts of phosphonic acids of the formula I is carried out, for example, by addition of an alkali or alkaline-earth metal hydroxide, carbonate or bicarbonate in a polar solvent, for example in ethanol, methanol or isopropanol.

The compounds of the formula II indicated and the further reactants in the synthesis are commercially available or accessible by syntheses which are well known from the literature to the person skilled in the art. The choice of suitable reaction conditions is standard to the person skilled in the art of synthesis.

It has also been observed that compounds of the formula I can have a stabilising effect on compositions. When used in corresponding products, the latter therefore also remain stable for longer and do not change their appearance. In particular, the efficacy of the ingredients, for example vitamins, is retained even in the case of application over extended periods or extended storage. This is, inter alia, particularly advantageous in the case of compositions for protecting the skin against the effect of UV rays since these cosmetics are subjected to particularly high stresses by UV radiation.

The positive effects of compounds of the formula I give rise to their particular suitability for use in cosmetic or pharmaceutical compositions.

The properties of compounds of the formula I should likewise be regarded as positive for use in foods or as food supplements or as functional food. The further explanations given for foods also apply correspondingly to food supplements and functional food.

The foods which can be enriched in accordance with the present invention with one or more compounds of the formula I include all materials which are suitable for consumption by animals or for consumption by humans, for example vitamins and provitamins thereof, fats, minerals or amino acids. (The foods may be solid, but also liquid, i.e. in the form of a beverage). The present invention accordingly furthermore relates to the use of a compound of the formula I as food additive for human or animal nutrition, and to compositions which are foods or food supplements and comprise corresponding vehicles.

Foods which can be enriched in accordance with the present invention with one or more compounds of the formula I are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods are corn or cereals from a single plant species and materials produced from plant species of this type, such as, for example, cereal syrup, rye flour, wheat flour or oat bran. Mixtures of foods of this type are also suitable for being enriched in accordance with the present invention with one or more compounds of the formula I, for example multivitamin preparations, mineral mixtures or sweetened juice. Further examples of foods which may be mentioned are food preparations, for example prepared cereals, biscuits, mixed drinks, foods prepared especially for children, such as yoghurt, diet foods, low-calorie foods or animal feeds.

The foods which can be enriched in accordance with the present invention with one or more compounds of the formula I thus include all edible combinations of carbohydrates, lipids, proteins, inorganic elements, trace elements, vitamins, water or active metabolites of plants and animals.

The foods which can be enriched in accordance with the present invention with one or more compounds of the formula I are preferably administered orally, for example in the form of meals, pills, tablets, capsules, powders, syrup, solutions or suspensions.

The foods according to the invention enriched with one or more compounds of the formula I can be prepared with the aid of techniques which are well known to the person skilled in the art.

Due to their action as antioxidants or free-radical scavengers, compounds of the formula I are also suitable as medicament ingredient, where they support or replace natural mechanisms which scavenge free radicals in the body. The compounds of the formula I can in some cases be compared in their action with free-radical scavengers, such as vitamin C. Compounds of the formula I can be used, for example, for the preventative treatment of inflammation and allergies of the skin and in certain cases for preventing certain types of cancer. Compounds of the formula I are particularly suitable for the preparation of a medicament for the treatment of inflammation, allergies and irritation, in particular of the skin. It is furthermore possible to prepare medicaments which act as vein tonic, as agent for increasing the strength of blood capillaries, as cuperose inhibitor, as inhibitor of chemical, physical or actinic erythemas, as agent for the treatment of sensitive skin, as decongestant, as dehydration agent, as slimming agent, as anti-wrinkle agent, as stimulators of the synthesis of components of the extracellular matrix, as strengthening agent for improving skin elasticity, and as anti-ageing agent. Furthermore, compounds of the formula I which are preferred in this connection exhibit anti-allergic and anti-inflammatory and anti-irritative actions. They are therefore suitable for the preparation of medicaments for the treatment of inflammation or allergic reactions.

The invention is explained in greater detail below with reference to examples. The invention can be carried out throughout the scope claimed and is not restricted to the examples given here.

EXAMPLES

Example 1

Preparation of [(7,8-dihydroxy-4-oxo-4H-chromen-3-yl)-hydroxymethyl]phosphonic acid

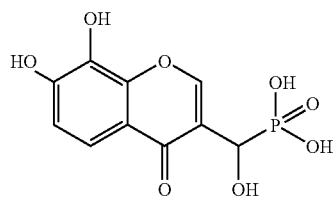

Procedure:
1st Step:

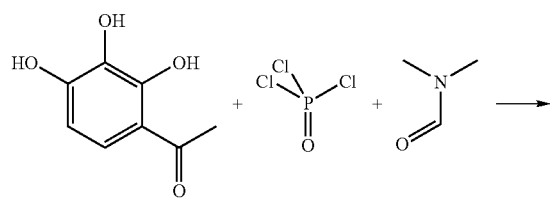

-continued

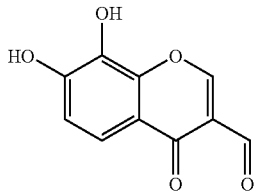

10 g (59.5 mmol) of 2,3,4-trihydroxyacetophenone are dissolved in 120 ml of N,N-dimethylformamide, initially introduced at −50° C. (dry ice/ethanol), and 21.8 ml (237.9 mmol) of phosphoryl chloride are subsequently slowly added dropwise over about 30 min.

The clear solution is subsequently stirred at −20° C. for 30 min., the cold bath is removed, and stirring is continued overnight at room temperature. The complete reaction solution is poured into about 200 ml of ice/water, and the resultant suspension is filtered with suction and rinsed with water. The solid obtained is dried overnight in a vacuum drying cabinet at 45° C. and 200 mbar.

$^1$H NMR (500 MHz) in DMSO δ (ppm):.7.0 (d, 1H), 7.5 (d, 1H), 8.8 (s, 1H), 10.1 (s, 1H), 10.6 (bs, OH).

$^{13}$C NMR (75 MHz) in DMSO δ (ppm): 114.8, 115.5, 117.7, 119, 133.6, 146.3, 151.3, 162.3, 174.5, 188.6.

ESI-MS (m/e): 206.

2nd Step:

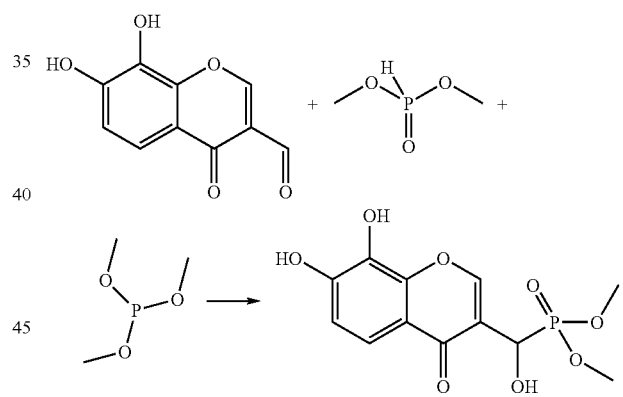

4.3 g (20.858 mmol) of 7,8-dihydroxy-4-oxo-4H-1-benzopyran-3-carbaldehyde are suspended in 19 ml of dimethyl phosphonate under argon at RT (RT=room temperature), and a few drops of trimethyl phosphite are then added. The suspension is then stirred at 85° C. for 1.5 h, and stirring is continued overnight at RT.

For work-up, the reaction solution is added to 200 ml of dichloromethane and stirred at RT for 1 h. The phosphonate precipitates as a solid.

$^1$H NMR (250 MHz) in DMSO δ (ppm):.3.6 (d, 3H), 3.7 (d, 3H), 5.25 (bd, 1 H), 6.2 (bs, OH), 6.95 (d, 1H), 7.45 (d, 1H), 8.25 (d, 1H), 9.45 (bs, OH), 10.53 (bs, OH).

$^{13}$C NMR (63 MHz) in DMSO δ (ppm): 53(d), 53.4(d), 54.8, 58.1, 60.8, 114.4, 115.4, 116.5, 120.6, 133.0, 146.6, 150.3, 155.2, 174.1.

$^{31}$P NMR (100 MHz) in DMSO δ (ppm): 25.3.

3rd Step:

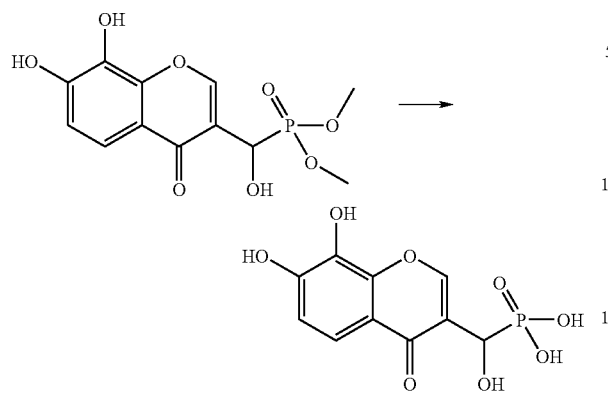

5.2 g (16.44 mmol) of dimethyl [(7,8-dihydroxy-4-oxo-4H-1-benzopyran-3-yl)hydroxymethyl]phosphonate are suspended in 40 ml of 2 N hydrochloric acid and warmed to the boiling point. After complete hydrolysis, the reaction solution is cooled to RT, during which the phosphonic acid precipitates as a solid. After being filtered off, the product is washed with a little water and dried.

$^1$H NMR (250 MHz) in DMSO δ (ppm): 5.0 (d, 1H), 6.9 (d, 1H), 7.4 (d, 1H), 8.2 (d, 1H), 9.4 (bs, OH), 10.25 (bs, OH).
$^{13}$C NMR (63 MHz) in DMSO δ (ppm): 59.1, 61.8, 114.2, 115.4, 116.8, 121.9, 132.9, 146.5, 150.0, 154.7.
$^{31}$P NMR (100 MHz) in DMSO δ (ppm): 18.8.
ESI-MS (m/e): 288.

Example 2

The following are reacted analogously to Example 1:
a) 2,4-Dihydroxy-3-methylacetophenone with phosphoryl chloride in dimethylformamide and subsequently with dimethyl phosphonate, giving dimethyl [(7-hydroxy-8-methyl-4-oxo-4H-chromen-3-yl)hydroxymethyl]phosphonate.
$^1$H NMR (300 MHz) in DMSO δ (ppm): 2.25 (s, 3H), 3.66 (d, 3H), 3.74 (d, 3H), 5.27 (d, 1H), 7.03 (d, 1H), 7.81 (d, 1H), 8.3 (d, 1H).
Ester hydrolysis gives [(7-hydroxy-8-methyl-4-oxo-4H-chromen-3-yl)-hydroxymethyl]phosphonic acid.
$^1$H NMR (300 MHz) in DMSO δ (ppm): 2.21 (s, 3H), 5.0 (d, 1H), 6.98 (d, 1H), 7.76 (d, 1H), 8.23 (d, 1H).
b) 2,4-Dihydroxyacetophenone with phosphoryl chloride in dimethylformamide and subsequently with dimethyl phosphonate, giving dimethyl [(7-hydroxy-4-oxo-4H-chromen-3-yl)hydroxymethyl]phosphonate.
$^1$H NMR (500 MHz) in DMSO δ (ppm): 3.63 (d, 3H), 3.72 (d, 3H), 5.24 (d, 1H), 6.87 (d, 1H), 6.95 (dd, 1H), 7.93 (d, 1H), 8.21 (d, 1H).
Ester hydrolysis gives [(7-hydroxy-4-oxo-4H-chromen-3-yl)hydroxymethyl]-phosphonic acid.
$^1$H NMR (300 MHz) in DMSO δ (ppm): 5.18 (d, 1H), 6.9 (d, 1H), 6.97 (dd, 1H), 7.97 (d, 1H), 8.21 (d, 1H).
c) 2,4-Dihydroxyacetophenone with phosphoryl chloride in dimethylformamide and subsequently with diethyl phosphonate, giving diethyl [7-hydroxy-4-oxo-4H-chromen-3-yl)hydroxymethyl]phosphonate.
d) 2,5-Dihydroxyacetophenone with phosphoryl chloride in dimethylformamide and subsequently with dimethyl phosphonate, giving dimethyl [6-hydroxy-4-oxo-4H-chromen-3-yl)hydroxymethyl]phosphonate.

$^1$H NMR (300 MHz) in DMSO δ (ppm):.3.62 (d, 3H), 3.71 (d, 3H), 5.75 (d, 1H), 7.23 (dd, 1H), 7.35 (d, 1H), 7.49 (d, 1H), 8.27 (d, 1H).
Ester hydrolysis gives [(6-hydroxy-4-oxo-4H-chromen-3-yl)hydroxymethyl]-phosphonic acid.
$^1$H NMR (300 MHz) in DMSO δ (ppm): 5.2 (d, 1H), 7.22 (dd, 1H), 7.33 (d, 1H), 7.51 (d, 1H), 8.24 (d, 1H).
e) 2-Hydroxy-5-methoxyacetophenone with phosphoryl chloride in dimethylformamide and subsequently with dimethyl phosphonate, giving dimethyl [6-methoxy-4-oxo-4H-chromen-3-yl)hydroxymethyl]phosphonate.
$^1$H NMR (300 MHz) in DMSO δ (ppm): 3.62 (d, 3H), 3.71 (d, 3H), 3.83 (s, 3H), 5.28 (d, 1H), 7.35 (dd, 1H), 7.44 (d, 1H), 7.54 (d, 1H), 8.29 (d, 1H).
Ester hydrolysis gives [(6-methoxy-4-oxo-4H-chromen-3-yl)hydroxymethyl]-phosphonic acid.
$^1$H NMR (300 MHz) in DMSO δ (ppm): 3.84 (s, 3H), 5.1 (d, 1H), 7.36 (dd, 1H), 7.44 (d, 1H), 7.56 (d, 1H), 8.26 (d, 1H).
f) 2,5-Dihydroxyacetophenone with phosphoryl chloride in dimethylformamide and subsequently with dibutyl phosphonate, giving dibutyl [6-hydroxy-4-oxo-4H-chromen-3-yl)hydroxymethyl]phosphonate.
g) 2,3,4-Trihydroxyacetophenone with phosphoryl chloride in dimethylformamide and subsequently with didodecyl phosphonate, giving didodecyl [(7,8-dihydroxy-4-oxo-4H-chromen-3-yl)hydroxymethyl]phosphonate. Ester hydrolysis gives [(7,8-dihydroxy-4-oxo-4H-chromen-3-yl)hydroxy-methyl]phosphonic acid.
h) 2,3,4-Trihydroxyacetophenone with phosphoryl chloride in dimethylformamide and subsequently with dioctadecyl phosphonate, giving dioctadecyl [7,8-dihydroxy-4-oxo-4H-chromen-3-yl)hydroxymethyl]phosphonate.

Example 3

[(6-Hydroxy-4-oxo-4H-chromen-3-yl)hydroxymethyl]phosphonic acid, prepared in accordance with Example 2d), is dissolved in ethanol, and a 1 M solution of KOH is subsequently added until a solid precipitates, giving the potassium salt of [(6-hydroxy-4-oxo-4H-chromen-3-yl)hydroxymethyl]phosphonic acid.

Example 4

Preparation of [(6-hydroxy-4-oxo-4H-chromen-3-yl)-methyl]phosphonic acid

[(6-Hydroxy-4-oxo-4H-chromen-3-yl)hydroxymethyl]phosphonic acid (10 mmol), prepared in accordance with Example 2d), hydroiodic acid (57%) (38 mmol) and red phosphorus (20 mmol) are added to acetic acid (100 ml). This mixture is heated at 110-115° C. until the reaction is complete. The hot reaction mixture is subsequently filtered, and the residue is washed twice with 10 ml of hot acetic acid. The filtrate is decolourised by addition of aqueous Na$_2$SO$_3$ solution. A solid precipitates at temperatures of 6 to 10° C. After filtration, the solid is washed with a little cold water and dried, giving [(6-hydroxy-4-oxo-4H-chromen-3-yl)methyl]phosphonic acid.

$^1$H NMR (300 MHz) in DMSO δ (ppm):.2.9 (d, 2H), 7.25 (dd, 1H), 7.38 (d, 1H), 7.5 (d, 1H), 8.2 (d, 1H).
$^{31}$P NMR (100 MHz) in DMSO δ (ppm): 16.8.
MS (m/e): 222 (M$^+$).

Example 5

Antioxidative properties of [(7,8-dihydroxy-4-oxo-4H-chromen-3-yl)hydroxymethyl]phosphonic acid, prepared in accordance with Example 1 a) The basis for the determination of the antioxidative efficacy is the so-called DPPH test, as described in Bünger et al. [Buenger, J., Ackermann, H., Jentzsch, A., Mehling, A., Pfizner, I., Reiffen, K.-A., Schroeder, K.-R., and Wollenweber U., An interlaboratory comparison of methods used to assess antioxidant potentials, *Int. J. Cosm. Sci.*, 28 (2006) 1-12]. The anti-oxidative efficacy of [(7,8-dihydroxy-4-oxo-4H-chromen-3-yl)hydroxy-methyl]phosphonic acid is determined in the DPPH test. The $EC_{50}$ value is 0.24 µmol/l and reflects excellent free-radical scavenger properties.

b) The basis for the determination of the antioxidative efficacy is also the so-called TEAC assay (trolox equivalent antioxidant activity assay), as described in Buenger et al. [Buenger, J., Ackermann, H., Jentzsch, A., Mehling, A., Pfizner, I., Reiffen, K.-A., Schroeder, K.-R. and Wollenweber U., An interlaboratory comparison of methods used to assess antioxidant potentials, *Int. J. Cosm. Sci.*, 28 (2006), 1-12].

ABTS [2,2'-azinobis(3-ethylbenzothiazoline-6-sulfonic acid)] reacts with potassium peroxodisulfate by generating a stable free-radical cation which absorbs at 734 nm. The antioxidant measured reduces the free-radical cation and thus causes a weakening of the absorption capacity at 734 nm. The absorption is measured after a fixed time span of 6 minutes. The anti-oxidative potential of the substance measured is indicated as activity compared with trolox. The substance measured may be present dissolved in water or ethanol during the measurement.

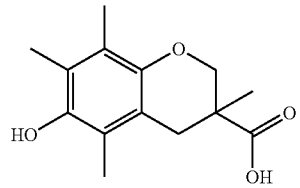

Trolox

The value measured is 0.93 compared with 1.0 for trolox, i.e. the compound according to the invention exhibits a high antioxidative potential.

Example 6

Compositions

Illustrative formulations of cosmetic compositions which comprise compounds according to Example 1 or 2 are indicated below. In addition, the INCI names of the commercially available compounds are indicated.

UV-Pearl, OMC stands for the composition having the INCI name:

Water (for EU: Aqua), Ethylhexyl Methoxycinnamate, Silica, PVP, Chlorphenesin, BHT; this composition is commercially available from Merck KGaA, Darmstadt, under the name Eusolex®UV Pearl™OMC.

The other UV-Pearls indicated in the tables each have an analogous composition, with OMC having been replaced by the UV filters indicated.

TABLE 1

| W/O emulsions (data in % by weight) | | | | | | | | | | |
|---|---|---|---|---|---|---|---|---|---|---|
| | 1-1 | 1-2 | 1-3 | 1-4 | 1-5 | 1-6 | 1-7 | 1-8 | 1-9 | 1-10 |
| Titanium Dioxide | | 2 | 5 | | | | | | | 3 |
| [(7,8-Dihydroxy-4-oxo-4H-chromen-3-yl)hydroxymethyl]phosphonic acid | 5 | 3 | 2 | 1 | 2 | | | | 1 | 1 |
| [(6-Hydroxy-4-oxo-4H-chromen-3-yl)hydroxymethyl]phosphonic acid | | | | | | 1 | 2 | 1 | | |
| Zinc Oxide | | | | | | | | 5 | 2 | |
| UV-Pearl, OMC | 30 | 15 | 15 | 15 | 15 | 15 | 15 | 15 | 15 | 15 |
| Polyglyceryl 3-Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

| | 1-11 | 1-12 | 1-13 | 1-14 | 1-15 | 1-16 | 1-17 | 1-18 |
|---|---|---|---|---|---|---|---|---|
| Titanium Dioxide | 3 | | 2 | | 3 | | 2 | 5 |
| Benzylidene Malonate Polysiloxane | | 1 | 0.5 | | | | | |
| Methylene Bis-Benzotriazolyl Tetramethylbutylphenol | 1 | 1 | 0.5 | | | | | |
| [(7,8-Dihydroxy-4-oxo-4H-chromen-3-yl)hydroxymethyl]phosphonic acid | 5 | 3 | 2 | 5 | 1 | 3 | 7 | 2 |

TABLE 1-continued

| W/O emulsions (data in % by weight) | | | | | | | | |
|---|---|---|---|---|---|---|---|---|
| Polyglyceryl 3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Dicocoyl Pentaerythrityl Citrate (and) Sorbitan Sesquioleate (and) Cera Alba (and) Aluminium Stearate | | | | | 6 | 6 | 6 | 6 |
| PEG-7 Hydrogenated Castor Oil | | | | | 1 | 1 | 1 | 1 |
| Zinc Stearate | | | | | 2 | 2 | 2 | 2 |
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Tromethamine | | | | | 1 | 1 | 1 | 1 |
| Glycerin | | | | | 5 | 5 | 5 | 5 |
| Allantoin | | | | | 0.2 | 0.2 | 0.2 | 0.2 |
| Water | to 100 | to 100 | to 100 | to 100 | to 100 | to 100 | to 100 | to 100 |

TABLE 2

| O/W emulsions, data in % by weight | | | | | | | | | | |
|---|---|---|---|---|---|---|---|---|---|---|
| | 2-1 | 2-2 | 2-3 | 2-4 | 2-5 | 2-6 | 2-7 | 2-8 | 2-9 | 2-10 |
| Titanium Dioxide | | 2 | 5 | | | | | | | 3 |
| Methylene Bis-Benzotriazolyl Tetramethylbutylphenol | | | | | | 1 | 2 | 1 | | |
| Dimethyl [(7,8-dihydroxy-4-oxo-4H-chromen-3-yl)hydroxymethyl]phosphonate | 1 | 3 | | 3 | 2 | 5 | | 5 | 3 | 1 |
| [(7,8-Dihydroxy-4-oxo-4H-chromen-3-yl)-hydroxymethyl]phosphonic acid | 5 | 5 | 5 | 5 | 5 | 5 | 5 | 5 | 5 | 5 |
| [(6-Hydroxy-4-oxo-4H-chromen-3-yl)-hydroxymethyl]phosphonic acid | 1 | 5 | 4 | | 6 | | 7 | | 2 | 1 |
| 4-Methylbenzylidene Camphor | 2 | | 3 | | 4 | | 3 | | 2 | |
| BMDBM | 1 | 3 | | 3 | 3 | | 3 | 3 | 3 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| Persea Gratissima | | | | | | | | | | |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Tromethamine | | | 1.8 | | | | | | | |
| Glycerin | | | | | | | | | | |
| Water | to 100 | to 100 | to 100 | to 100 | to 100 | to 100 | to 100 | to 100 | to 100 | to 100 |
| | 2-11 | 2-12 | 2-13 | 2-14 | 2-15 | 2-16 | 2-17 | 2-18 | | |
| Titanium Dioxide | 3 | | 2 | | | | 2 | 5 | | |
| Benzylidene Malonate Polysiloxane | | 1 | 0.5 | | | | | | | |
| Methylene Bis-Benzotriazolyl Tetramethylbutylphenol | 1 | 1 | 0.5 | | | | | | | |

TABLE 2-continued

O/W emulsions, data in % by weight

| | | | | | | | | |
|---|---|---|---|---|---|---|---|---|
| Dimethyl [(7,8-dihydroxy-4-oxo-4H-chromen-3-yl)hydroxymethyl]phosphonate | 5 | 5 | 5 | 5 | 5 | 5 | 5 | 5 |
| Zinc Oxide | | | 2 | | | | | |
| UV-Pearl, OMC | 15 | 15 | 15 | 30 | 30 | 30 | 15 | 15 |
| 4-Methylbenzylidene Camphor | | | | 3 | | | | |
| BMDBM | | | | 1 | | | | |
| Phenylbenzimidazole Sulfonic Acid | | | | | 4 | | | |
| Stearyl Alcohol (and) Steareth-7 (and) Steareth-10 | 3 | 3 | 3 | 3 | | | | |
| Glyceryl Stearate (and) Ceteth-20 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |
| Stearic Acid | | | | | 2 | 2 | 2 | 2 |
| *Persea Gratissima* | | | | | 8 | 8 | 8 | 8 |
| Propylparaben | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 |
| Trometamine | | | | | 1.8 | | | |
| Glycerin | | | | | 3 | 3 | 3 | 3 |
| Water | to 100 | to 100 | to 100 | to 100 | to 100 | to 100 | to 100 | to 100 |

TABLE 3

Gels, data in % by weight

| | 3-1 | 3-2 | 3-3 | 3-4 | 3-5 | 3-6 | 3-7 | 3-8 | 3-9 | 3-10 |
|---|---|---|---|---|---|---|---|---|---|---|
| a = aqueous gel | | | | | | | | | | |
| Titanium Dioxide | | 2 | 5 | | | | | | | 3 |
| [(6-Hydroxy-4-oxo-4H-chromen-3-yl)-hydroxymethyl]phosphonic acid | | | | 1 | 2 | | | | 1 | 1 |
| [(6-Hydroxy-4-oxo-4H-chromen-3-yl)-hydroxymethyl]phosphonic acid, potassium salt | 1 | 3 | | 2 | | 5 | | 5 | 2 | |
| [(7,8-Dihydroxy-4-oxo-4H-chromen-3-yl)-hydroxymethyl]phosphonic acid | 5 | 5 | 5 | 5 | 5 | 5 | 5 | 5 | 5 | 5 |
| [(7,8-Dihydroxy-4-oxo-4H-chromen-3-yl)-hydroxymethyl]phosphonic acid, potassium salt | 1 | 5 | 4 | | 6 | | 7 | | 2 | 1 |
| Benzylidene Malonate Polysiloxane | | | 1 | 1 | 2 | | | | 1 | 1 |
| Methylene Bis-Benzotriazolyl Tetramethylbutylphenol | | 1 | | | | 1 | 2 | 1 | | |
| Zinc Oxide | | | | 2 | | | | 5 | 2 | |
| UV-Pearl, Ethylhexyl Methoxycinnamate | 30 | 15 | 15 | 15 | 15 | 15 | 15 | 15 | 15 | 15 |
| 4-Methylbenzylidene Camphor | | | | | 2 | | | | | |
| Butylmethoxydibenzoylmethane | | 1 | | | | | | | | |
| Phenylbenzimidazole Sulfonic Acid | | | 4 | | | | | | | |
| *Prunus Dulcis* | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparaben | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 |
| Trometamine | | | 1.8 | | | | | | | |
| Water | to 100 | to 100 | to 100 | to 100 | to 100 | to 100 | to 100 | to 100 | to 100 | to 100 |

The invention claimed is:
1. A compound of formula I

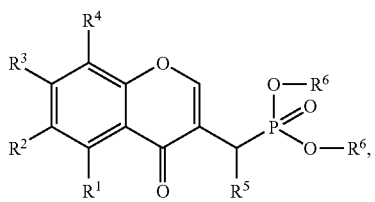

where
R$^1$ to R$^3$ each, independently of one another, denote H, hydroxyl or alkoxy having 1 to 8 C atoms,
R$^4$ denotes alkyl having 1 to 4 C atoms, H, hydroxyl or alkoxy having 1 to 8 C atoms,
R$^5$ denotes H or hydroxyl, and
R$^6$ denotes H or alkyl having 1 to 18 C atoms,
or a salt thereof,
but where all R$^1$ to R$^4$ together cannot be equal to H.

2. A compound according to claim 1, wherein R$^5$ denotes hydroxyl.

3. A process for preparing a compound of formula I according to claim 1, in which R$^6$, independently of one another, denotes alkyl having 1 to 18 C atoms and R$^5$=OH, comprising reacting a compound of formula II

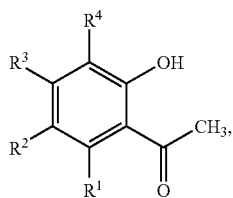

where R$^1$ to R$^4$ have one of the meanings provided for the compound of formula I, with POCl$_3$, phosgene or trifluoro-sulfonic anhydride and an arylalkyl-, diaryl- or dialkylformamide to give an intermediate compound of formula III

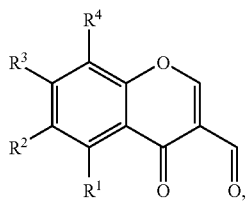

where R$^1$ to R$^4$ have one of the meanings provided for the compound of formula I,
and subsequently reacting the compound of formula III with a dialkyl phosphonate.

4. A process for preparing a compound of formula I according to claim 1, in which R$^6$ denotes H,
comprising reacting a compound of formula II

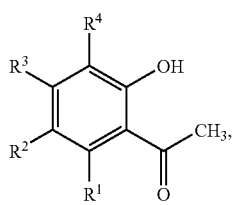

where R$^1$ to R$^4$ have one of the meanings provided for the compound of formula I, with POCl$_3$, phosgene or trifluorosulfonic anhydride and an arylalkyl-, diaryl- or dialkylformamide to give an intermediate compound of formula III

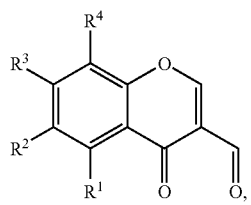

where R$^1$ to R$^4$ have one of the meanings provided for the compound of formula I, and subsequently reacting the compound of formula III with a dialkyl phosphonate, and then carrying out an ester hydrolysis, and the compound obtained is optionally converted into a salt.

5. A process for preparing a compound of formula I according to claim 1, in which R$^5$ denotes H,
comprising reacting a compound of formula II

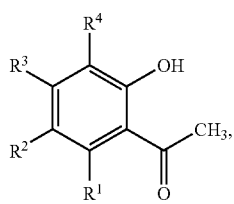

where R$^1$ to R$^4$ have one of the meanings provided for the compound of formula I, with POCl$_3$, phosgene or trifluorosulfonic anhydride and an arylalkyl-, diaryl- or dialkylformamide to give an intermediate compound of formula III

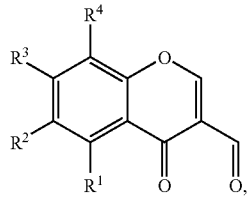

where R$^1$ to R$^4$ have one of the meanings provided for the compound of formula I, and subsequently reacting the compound of formula III with a dialkyl phosphonate, and then carrying out an ester hydrolysis, and
the compound obtained is optionally converted into a salt, and then carrying out a reduction.

6. A composition comprising at least one compound of formula I according to claim 1 and a pharmaceutically, cosmetically, dermatologically, food or food supplementally acceptable additional ingredient.

7. A composition according to claim 6, in which the at least one compound of formula I is present in an amount of 0.01% by weight to 20% by weight.

8. A composition according to claim 6, comprising one or more further antioxidants and/or vitamins.

9. A composition according to claim 6, comprising one or more UV filters.

10. A composition according to claim 6, which is a food or food supplement and comprises a vehicle which is suitable for foods or food supplements.

11. A composition according to claim 6, comprising a vehicle which is suitable for pharmaceutical, dermatological or cosmetic applications.

12. A process for preparing a composition according to claim 6, comprising mixing at least one compound of formula I with a vehicle which is suitable pharmaceutically, cosmetically or dermatologically or for foods.

13. A process for preparing a composition having antioxidant properties, comprising mixing into said composition a compound of formula I according to claim 1.

14. A method for exerting a protective action against oxidative stress on body cells and/or countering ageing of the skin or contributing to a reduction in the consequences of skin ageing comprising administering an effective amount of a compound of claim 1 to a subject in need thereof.

15. A food additive for human or animal nutrition, comprising a compound of claim 1.

16. A composition according to claim 6, in which the at least one compound of formula I is present in an amount of 0.1% by weight to 10% by weight.

17. A compound according to claim 1, wherein
$R^1$ is H,
$R^2$ and $R^3$ are each, independently of one another, hydroxyl,
$R^5$ is hydroxyl, and
$R^6$ is H or methyl.

18. A compound, which is
[(R7,8-dihydroxy-4-oxo-4H-chromen-3-yl)hydroxymethyl]phosphonic acid,
[(7-hydroxy-8-methyl-4-oxo-4H-chromen-3-yl)hydroxymethyl]phosphonic acid,
[(7-hydroxy-4-oxo-4H-chromen-3-yl)hydroxymethyl] phosphonic acid,
[(6-hydroxy-4-oxo-4H-chromen-3-yl)hydroxymethyl] phosphonic acid,
[(6-methoxy-4-oxo-4H-chromen-3-yl)hydroxymethyl] phosphonic acid,
[(7,8-dihydroxy-4-oxo-4H-chromen-3-yl)hydroxymethyl]phosphonic acid,
[(6-hydroxy-4-oxo-4H-chromen-3-yl)methyl]phosphonic acid,
potassium salt of [(6-hydroxy-4-oxo-4H-chromen-3-yl)hydroxymethyl]phosphonic acid,
potassium salt of [(7,8-Dihydroxy-4-oxo-4H-chromen-3-yl) hydroxymethyl]phosphonic acid,
dimethyl [(7-hydroxy-8-methyl-4-oxo-4H-chromen-3-yl) hydroxymethyl]phosphonate,
dimethyl [(7-hydroxy-4-oxo-4H-chromen-3-yl)hydroxymethyl]phosphonate,
diethyl [(7-hydroxy-4-oxo-4H-chromen-3-yl)hydroxymethyl]phosphonate,
dimethyl [(6-hydroxy-4-oxo-4H-chromen-3-yl)hydroxymethyl]phosphonate,
dimethyl [(6-methoxy-4-oxo-4H-chromen-3-yl)hydroxymethyl]phosphonate,
dibutyl [(6-hydroxy-4-oxo-4H-chromen-3-yl)hydroxymethyl]phosphonate,
didodecyl [(7,8-dihydroxy-4-oxo-4H-chromen-3-yl)hydroxymethyl]phosphonate, or
dioctadecyl [(7,8-dihydroxy-4-oxo-4H-chromen-3-yl)hydroxymethyl]phosphonate.

19. A pharmaceutical, cosmetic, or dermatologic composition or a food or food supplement, comprising at least one compound of claim 18 and a pharmaceutically, cosmetically, dermatologically, food or food supplementally acceptable additional ingredient.

* * * * *

UNITED STATES PATENT AND TRADEMARK OFFICE
CERTIFICATE OF CORRECTION

PATENT NO.        : 8,052,963 B2
APPLICATION NO.   : 12/447369
DATED             : November 8, 2011
INVENTOR(S)       : Christophe Carola et al.

It is certified that error appears in the above-identified patent and that said Letters Patent is hereby corrected as shown below:

Column 35, Line 36 reads: [(R7,8-dihydroxy-4-oxo-4H-chromen-3-yl)hydroxym-" should read -- [(7,8-dihydroxy-4-oxo-4H-chromen-3-yl)hydroxym- --.

Signed and Sealed this
Twenty-seventh Day of March, 2012

David J. Kappos
*Director of the United States Patent and Trademark Office*